United States Patent
Bailey

(10) Patent No.: US 12,042,229 B2
(45) Date of Patent: Jul. 23, 2024

(54) PATIENT-SPECIFIC ORTHOPEDIC IMPLANTS AND PROCEDURES USING BONE DENSITY

(71) Applicant: Zimmer, Inc., Warsaw, IN (US)

(72) Inventor: Kirk J. Bailey, Rochester, IN (US)

(73) Assignee: Zimmer, Inc., Warsaw, IN (US)

( * ) Notice: Subject to any disclaimer, the term of this patent is extended or adjusted under 35 U.S.C. 154(b) by 345 days.

(21) Appl. No.: 17/549,428

(22) Filed: Dec. 13, 2021

(65) Prior Publication Data

US 2022/0183758 A1 Jun. 16, 2022

Related U.S. Application Data

(60) Provisional application No. 63/125,266, filed on Dec. 14, 2020.

(51) Int. Cl.
*A61B 34/10* (2016.01)
*A61B 34/00* (2016.01)
(Continued)

(52) U.S. Cl.
CPC .............. *A61B 34/10* (2016.02); *A61B 34/25* (2016.02); *A61B 34/30* (2016.02); *A61B 90/37* (2016.02);
(Continued)

(58) Field of Classification Search
CPC ......... A61B 34/10; A61B 34/25; A61B 34/30; A61B 90/37
See application file for complete search history.

(56) References Cited

U.S. PATENT DOCUMENTS

| 8,884,618 B2 | 11/2014 | Mahfouz |
| 9,675,461 B2 | 6/2017 | Mahfouz |

(Continued)

OTHER PUBLICATIONS

Kubicek et al., Recent Trends, Technical Concepts and Components of Computer-Assisted Orthopedic Surgery Systems: A Comprehensive Review, Department of Cybernetics and Biomedical Engineering, VSB-Technical University of Ostrava, FEECS, 708 00 Ostrava-Poruba, Czech Republic, Received: Sep. 20, 2019 (Year: 2019).*

(Continued)

*Primary Examiner* — Hugh Maupin
(74) *Attorney, Agent, or Firm* — SCHWEGMAN LUNDBERG & WOESSNER, P.A.

(57) ABSTRACT

A method of implanting a prosthetic component using bone density information comprises positioning a bone density reference proximate a patient, obtaining two-dimensional x-ray images of a bone of the patient including the bone density reference, determining a density of the bone from the bone density reference in the two-dimensional x-ray images, superimposing the density of the bone into a three-dimensional mean bone model to generate a patient-specific mean bone model, determining an interface between the bone and the prosthetic component based on bone density information of the patient-specific mean bone model, and implanting the prosthetic component in the bone at the interface. Determining the interface comprises evaluating bone density at the interface to place the prosthetic component, determining bone load threshold at the interface to avoid damaging the bone, and determining hardness for the prosthetic implant at the interface to avoid damaging the bone.

24 Claims, 8 Drawing Sheets

(51) Int. Cl.
*A61B 34/30* (2016.01)
*A61B 90/00* (2016.01)

(52) U.S. Cl.
CPC ... *A61B 2034/102* (2016.02); *A61B 2034/105* (2016.02); *A61B 2034/108* (2016.02); *A61B 2090/367* (2016.02); *A61B 2090/376* (2016.02)

(56) References Cited

U.S. PATENT DOCUMENTS

| | | | |
|---|---|---|---|
| 10,130,478 B2 | 11/2018 | Mahfouz | |
| 10,258,256 B2 | 4/2019 | Mahfouz | |
| 10,512,451 B2 | 12/2019 | Mahfouz | |
| 10,736,539 B2 | 8/2020 | Mahfouz | |
| 10,779,954 B1 | 9/2020 | Northcutt et al. | |
| 2008/0119719 A1* | 5/2008 | Ascenzi | G06T 7/0012 600/410 |
| 2015/0119987 A1* | 4/2015 | Davignon | A61F 2/389 703/1 |
| 2015/0328004 A1* | 11/2015 | Mafhouz | A61F 2/34 700/98 |
| 2017/0312035 A1 | 11/2017 | May et al. | |
| 2017/0319141 A1* | 11/2017 | Revie | A61B 5/1127 |
| 2019/0290361 A1* | 9/2019 | Shalayev | A61B 34/10 |
| 2020/0030036 A1* | 1/2020 | Forstein | A61B 34/10 |
| 2020/0074748 A1* | 3/2020 | de Almeida Barreto | G06T 19/20 |
| 2020/0405392 A1* | 12/2020 | Chen | G06T 17/20 |
| 2022/0125535 A1* | 4/2022 | Janna | A61B 90/50 |
| 2022/0160519 A1* | 5/2022 | Northcutt | A61F 2/447 |

OTHER PUBLICATIONS

Mahfouz, et al., "Automatic methods for characterization of sexual dimorphism of adult femora: distal femur", Computer Methods in Biomechanics and Biomedical Engineering, 2007, iFirst article, Taylor & Francis, GB, (2007), 1-10 pgs.

* cited by examiner

PATIENT-SPECIFIC ORTHOPEDIC IMPLANTS AND PROCEDURES USING BONE DENSITY

CLAIM OF PRIORITY

This application claims the benefit of U.S. Provisional Patent Application Ser. No. 63/125,266, filed on Dec. 14, 2020, the benefit of priority of which is claimed hereby, and which is incorporated by reference herein in its entirety.

TECHNICAL FIELD

The present disclosure is directed to systems, devices and methods for use in planning and performing arthroplasty procedures, such as those that are robotically-assisted. More particularly, the present disclosure is directed to using patient-specific anatomical information to improve prosthetic component fit and performance, such as those that involve patient-specific prosthetic components.

BACKGROUND

Imaging of anatomical features can be useful in preparing for and performing surgical procedures. For example, patient-specific instruments can be derived from patient imaging and robotic surgical systems can be configured to track anatomy of a patient based on registration with patient imaging.

Patient-specific instruments have been successfully deployed for many surgical procedures. By creating three-dimensional (3D) models of anatomy of a patient from medical images, surgeries can be customized using virtual 3D surgical planning for specific patients. The virtual 3D surgical planning can be used to produce patient-specific prosthetics, implants, cutting guides and instruments. Typically, patient-specific devices include patient-specific surfaces that fit over the anatomy of the specific patient in a unique way to reduce misalignment and allow for precise replication of the planned surgery as compared to arthroplasty with conventional or standard instrumentation.

In robotic surgical systems, the shape of the anatomy in the patient imaging can be registered with another frame of reference, such as the physical space of an operating room where the robotic surgical system is located. Robotic surgical arms can be used to hold various instruments in place in a desired orientation relative to both the anatomy and operating room during a procedure so that movement of an instrument in the operating room relative to the anatomy can be tracked on the anatomic imaging based on movement of the robotic surgical arm.

There is a continuing desire to improve the planning and execution of orthopedic implant procedures to improve fit and performance for the needs of specific patients.

U.S. Pat. Nos. 10,736,539; 10,512,451; 10,258,256; and 10,130,478 to Mahfouz describe various methods of planning for orthopedic implant procedures.

OVERVIEW

The present inventor has recognized that, in surgical procedures planned using patient imaging, there is a desire to match the actual anatomy of the patient more closely, including soft tissue, to planning models derived from the patient imaging. Furthermore, the present inventor has recognized that there is a desire to reduce the occurrence of un-intended bone fragmentation during implantation of the prosthetic component and ill-fitting prosthetic implants.

The present inventor has recognized, among other things, that problems to be solved with traditional arthroplasty procedures involve evaluating soft tissue, such as bone density, pre-operatively and intra-operatively in order to improve bone resection placement and orthopedic implant selection. For example, problems associated with not knowing bone density or improperly assessing bone density involve 1) selecting suboptimal locations for altering the bone (e.g., locations where unhealthy or less dense bone engages the orthopedic implant), 2) damaging the bone of the patient during bone altering procedures (e.g., cutting, drilling, resecting), and 3) damaging the bone during implant placement (e.g., inserting the implant with excessive impact force).

The present subject matter can provide a solution to these and other problems, such as by providing solutions for allowing surgeons or surgical planners to obtain an indication of bone density pre-operatively. The solutions can include one or more of the following options: A) use surgery planning software to obtain bone density estimates and plot associated bone-altering locations; B) use of pre-operative bone density information to develop patient-specific implants; such as patient-specific implants made of materials having a hardness or modulus compatible with the hardness of the density of the bone of a specific patient; and C) use of pre-operative bone density information to augment robotically-assisted implant procedures, such as using robotic intelligence to limit impacting of implants with forces greater than bones of a specific density can safely withstand.

In an example, a method of implanting a prosthetic component using bone density information can comprise positioning a bone mineral density reference proximate a patient, obtaining two-dimensional x-ray images of a bone of the patient including the bone mineral density reference, determining a density of the bone from the bone mineral density reference in the two-dimensional x-ray images, superimposing the density of the bone into a three-dimensional mean bone model to generate a patient-specific mean bone model, determining an interface between the bone and the prosthetic component based on bone density information of the patient-specific mean bone model, and implanting the prosthetic component in the bone at the interface.

In an additional example, a method of generating an electronic surgical plan using a patient-specific bone density model can comprise obtaining two-dimensional x-ray images of a bone of a patient including a bone density reference object, determining bone density levels of the bone in each of the two-dimensional x-ray images from the bone density reference object, generating a three-dimensional bone model of the bone of the patient from the two-dimensional x-ray images, importing the bone density levels into the three-dimensional model to generate three-dimensional bone density information, superimposing the three-dimensional bone density information onto a three-dimensional mean bone model to generate the patient-specific bone density model, plotting an interface for a prosthetic component on the patient-specific bone density model, and saying a digital version of the electronic surgical plan in a computer-readable storage medium.

In another example, a method of electronically planning a surgical procedure for implanting a prosthetic component into a bone using bone density information to reduce fracture risk can comprise determining bone density of the bone in each of a plurality of two-dimensional x-ray images of the bone using a bone density reference object in the two-dimensional x-ray images, determining a three-dimensional bone density of the bone from the two-dimensional x-ray images, superimposing the three-dimensional bone density of the bone into an electronic three-dimensional mean bone model to generate an electronic patient-specific mean bone model, displaying the electronic patient-specific mean bone model on an electronic graphical display device, plotting an interface between the bone and the prosthetic component on the electronic patient-specific mean bone model in the electronic graphical display device, using the three-dimensional bone density on the electronic patient-specific mean bone model to determine a threshold impact load for the bone at the interface to avoid damaging the bone, and generating an electronic output of the threshold impact load.

DETAILED DESCRIPTION

Figure 1:
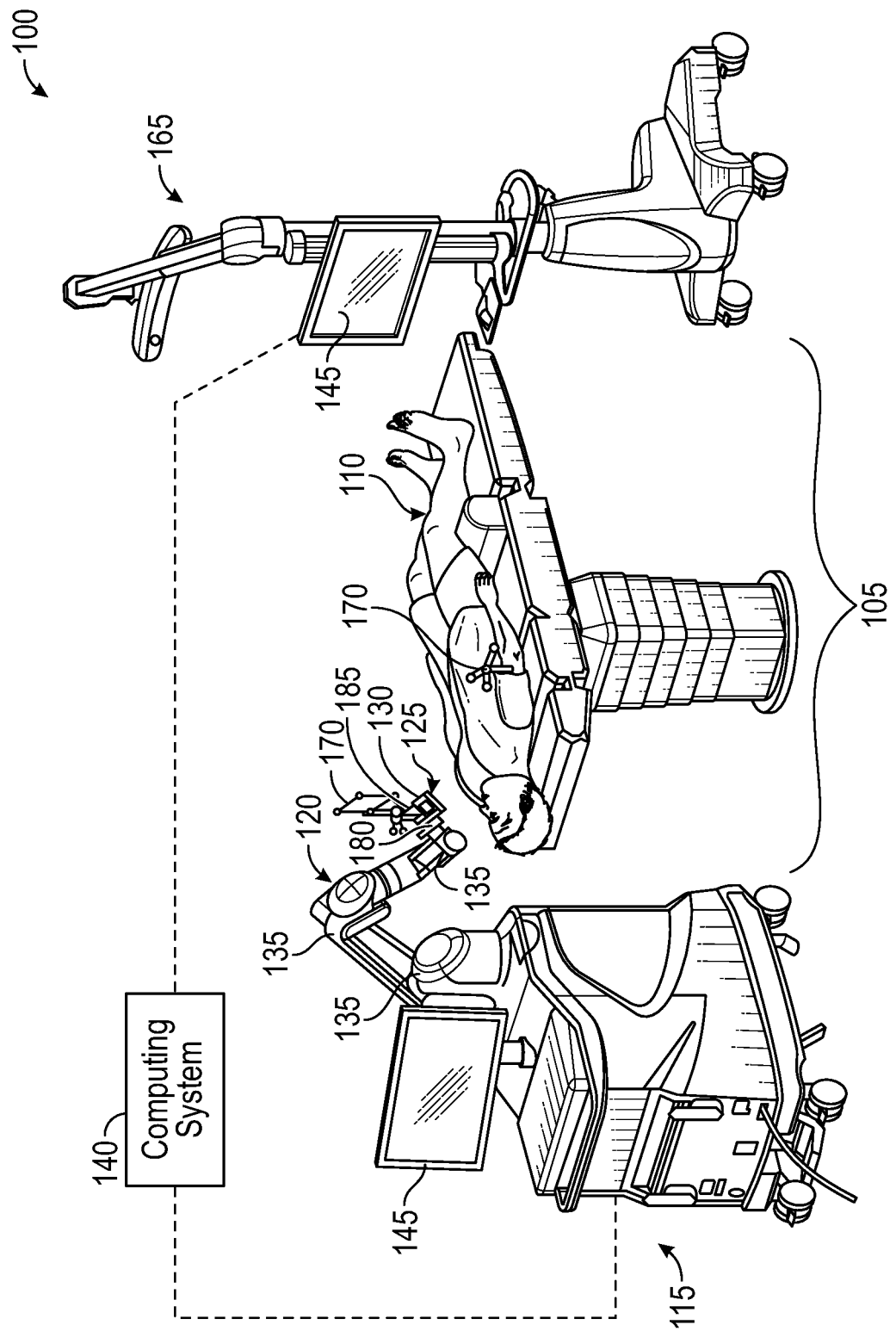
FIG. 1 is a diagrammatic view of an operating room including a robot-assisted surgical system comprising a robotic arm, a computing system and a tracking system with which the systems, devices and methods of the present disclosure can be implemented.

FIG. 1 illustrates surgical system 100 for operation on surgical area 105 of patient 110 in accordance with at least one example of the present disclosure. Surgical area 105 in one example can include a joint and, in another example, can be a bone. Surgical area 105 can include any surgical area of patient 110, including but not limited to the shoulder, head, elbow, thumb, spine, and the like. Surgical system 100 can also include robotic system 115 with one or more robotic arms, such as robotic arm 120. As illustrated, robotic system 115 can utilize only a single robotic arm. Robotic arm 120 can be a 6 degree-of-freedom (DOF) robot arm, such as the ROSA® robot from Medtech, a Zimmer Biomet Holdings, Inc. company. In some examples, robotic arm 120 can be cooperatively controlled with surgeon input on the end effector or surgical instrument, such as surgical instrument 125. In other examples, robotic arm 120 can operate autonomously. While not illustrated in FIG. 1, one or more positionable surgical support arms can be incorporated into surgical system 100 to assist in positioning and stabilizing instruments or anatomy during various procedures.

Each robotic arm 120 can rotate axially and radially and can receive a surgical instrument, or end effector, 125 at distal end 130. Surgical instrument 125 can be any surgical instrument adapted for use by the robotic system 115, including, for example, a guide tube, a holder device, a gripping device such as a pincer grip, a burring device, a reaming device, an impactor device such as a humeral head impactor, a pointer, a force-limiting device, a probe or the like. Surgical instrument 125 can be positionable by robotic arm 120, which can include multiple robotic joints, such as joints 135, that allow surgical instrument 125 to be positioned at any desired location adjacent or within a given surgical area 105. As discussed below, robotic arm 120 can be used with an instrument positioning device, e.g., instrument holder 200 (FIG. 2), to position an instrument in a known, desired or predetermined orientation relative to surgical area 105 based on a virtual coordinate system determined by computing system 140. Instrument holder 200 can be configured to limit force transmitted to the patient through the device to prevent or limit injury (e.g., bruising) to the patient or damage to a bone of the patient (e.g., cracking of bone).

Robotic system 115 can also include computing system 140 that can operate robotic arm 120 and surgical instrument 125. Computing system 140 can include at least memory, a processing unit, and user input devices, as will be described herein. Computing system 140 and tracking system 165 can also include human interface devices 145 for providing images for a surgeon to be used during surgery. Computing system 140 is illustrated as a separate standalone system, but in some examples computing system 140 can be integrated into robotic system 115. Human interface devices 145 can provide images, including but not limited to three-dimensional images of bones, a glenoid, joints, and the like. Human interface devices 145 can include associated input mechanisms, such as a touch screen, foot pedals, or other input devices compatible with a surgical environment.

Computing system 140 can receive pre-operative, intra-operative and post-operative medical images. These images can be received in any manner and the images can include, but are not limited to, computed tomography (CT) scans, magnetic resonance imaging (MRI), two-dimensional x-rays, three-dimensional x-rays, ultrasound, and the like. As discussed herein, these images can include, such as when obtained with reference bone density markers, bone density information that can be used to, for example, 1) determine locations for bone modifications in order to prepare the bone to receive a prosthetic device accounting for the location of less dense bone, 2) produce patient-specific prosthetic devices with patient-specific properties such as modulus, and 3) and operate in conjunction with instrument holder 200 to control force delivered to the patient. These images in one example can be sent via a server as tiles attached to an email. In another example the images can be stored on an external memory device such as a memory stick and coupled to a USB port of the robotic system to be uploaded into the processing unit. In yet other examples, the images can be accessed over a network by computing system 140 from a remote storage device or service.

After receiving one or more images, computing system 140 can generate one or more virtual models related to surgical area 105, such as a three-dimensional model incorporating bone density information. Alternatively, computer system 140 can receive virtual models of the anatomy of the patient prepared remotely. Specifically, a virtual model of the anatomy of patient 110 can be created by defining anatomical points within the image(s) and/or by fitting a statistical anatomical model to the image data. Additionally, the virtual model can be created using multiple orthogonal x-ray images of the anatomy of the patient merged together to form a three-dimensional model. The virtual model, along with virtual representations of implants, can be used for calculations related to the desired height, depth, inclination angle, or version angle of an implant, stem, surgical instrument, or the like related to be utilized in surgical area 105. In another procedure type, the virtual model can be utilized to determine insertion location, trajectory, insertion force (e.g., an insertion force ceiling to avoid adversely affecting bone structure of a specific patient) and depth for inserting an instrument. The virtual model can also be used to determine bone dimensions, implant dimensions, bone fragment dimensions, bone fragment arrangements, and the like. Any model generated, including three-dimensional models, can be displayed on human interface devices 145 for reference during a surgery or used by robotic system 115 to determine motions, actions, and operations of robotic arm 120 or surgical instrument 125. Known techniques for creating virtual bone models can be utilized, such as those discussed in U.S. Pat. No. 9,675,461, titled "Deformable articulating templates" or U.S. Pat. No. 8,884,618, titled "Method of generating a patient-specific bone shell" both by Mahfouz, as well as other techniques known in the art.

Computing system 140 can also communicate with tracking system 165 that can be operated by computing system 140 as a stand-alone unit. Surgical system 100 can utilize the Polaris optical tracking system from Northern Digital, Inc. of Waterloo, Ontario, Canada. Additionally, tracking system 165 can comprise the tracking system shown and described in Pub, No. US 2017/0312035, titled "Surgical System Having Assisted Navigation" to Brian M. May, which is hereby incorporated by this reference in its entirety. Tracking system 165 can monitor a plurality of tracking elements, such as tracking elements 170, affixed to objects of interest to track locations of multiple objects within the surgical field. Tracking system 165 functions to create a virtual three-dimensional coordinate system within the surgical field for tracking patient anatomy, surgical instruments, or portions of robotic system 115. Tracking elements 170 can be tracking frames including multiple IR reflective tracking spheres, or similar optically tracked marker devices. In one example, tracking elements 170 can be placed on or adjacent one or more bones of patient 110. In other examples, tracking elements 170 can be placed on robot robotic arm 120, surgical instrument 125, and/or an implant to accurately track positions within the virtual coordinate system associated with surgical system 100. In each instance tracking elements 170 can provide position data, such as patient position, bone position, joint position, robotic arm position, implant position, or the like.

Robotic system 115 can include various additional sensors and guide devices. For example, robotic system 115 can include one or more force sensors, such as force sensor 180. Force sensor 180 can provide additional force data or information to computing system 140 of robotic system 115. Force sensor 180 can be used by a surgeon to cooperatively move robotic arm 120. For example, force sensor 180 can be used to monitor impact or implantation forces during certain operations, such as insertion of an implant stem into a humeral canal. Monitoring forces can assist in preventing negative outcomes through force fitting components. In other examples, force sensor 180 can provide information on soft-tissue tension in the tissues surrounding a target joint. In certain examples, robotic system 115 can also include laser pointer 185 that can generate a laser beam or array that is used for alignment of implants during surgical procedures. Furthermore, robotic system 115 can use sensor data from instrument holder 200 (FIG. 2) to limit the force applied to bones by instruments based on the strength of the bone determined from bone density information.

In order to ensure that computing system 140 is moving robotic arm 120 in a known and fixed relationship to surgical area 105 and patient 110, the space of surgical area 105 and patient 110 can be registered to computing system 140 via a registration process involving registering fiducial markers attached to patient 110 with corresponding images of the markers in patient 110 recorded preoperatively or just prior to a surgical procedure. For example, a plurality of fiducial markers can be attached to patient 110, images of patient 110 with the fiducial markers can be taken or obtained and stored within a memory device of computing system 140. Subsequently, patient 110 with the fiducial markers can be moved into, if not already there because of the imaging, surgical area 105 and robotic arm 120 can touch each of the fiducial markers. Engagement of each of the fiducial markers can be cross-referenced with, or registered to, the location of the same fiducial marker in the images. In additional examples, patient 110 and medical images of the patient can be registered in real space using contactless methods, such as by using a laser rangefinder held by robotic arm 120 and a surface matching algorithm that can match the surface of the patient from scanning of the laser rangefinder and the surface of the patient in the medical images. As such, the real-world, three-dimensional geometry of the anatomy attached to the fiducial markers can be correlated to the anatomy in the images and movements of instruments 125 attached to robotic arm 120 based on the images will correspondingly occur in surgical area 105.

Subsequently, other instruments and devices attached to surgical system 100 can be positioned by robotic arm 120 into a known and desired orientation relative to the anatomy. For example, robotic arm 120 can be coupled to an instrument holder including an impact control device of the present disclosure. Robotic arm 120 can move the instrument holder and impact control device into different positions relative to anatomy of the patient such that an axis of the adjustable instrument holder extends along a desired orientation relative to the anatomy. The impact control devices of the present application can enable surgical system 100 to know the force with which an instrument is being delivered to a patient, relative to the instrument holder (e.g., mass of instrument*velocity of instrument), so that the force delivered to the patient can be limited in order to prevent undesirable outcomes and to preserve bone.

Figure 2:
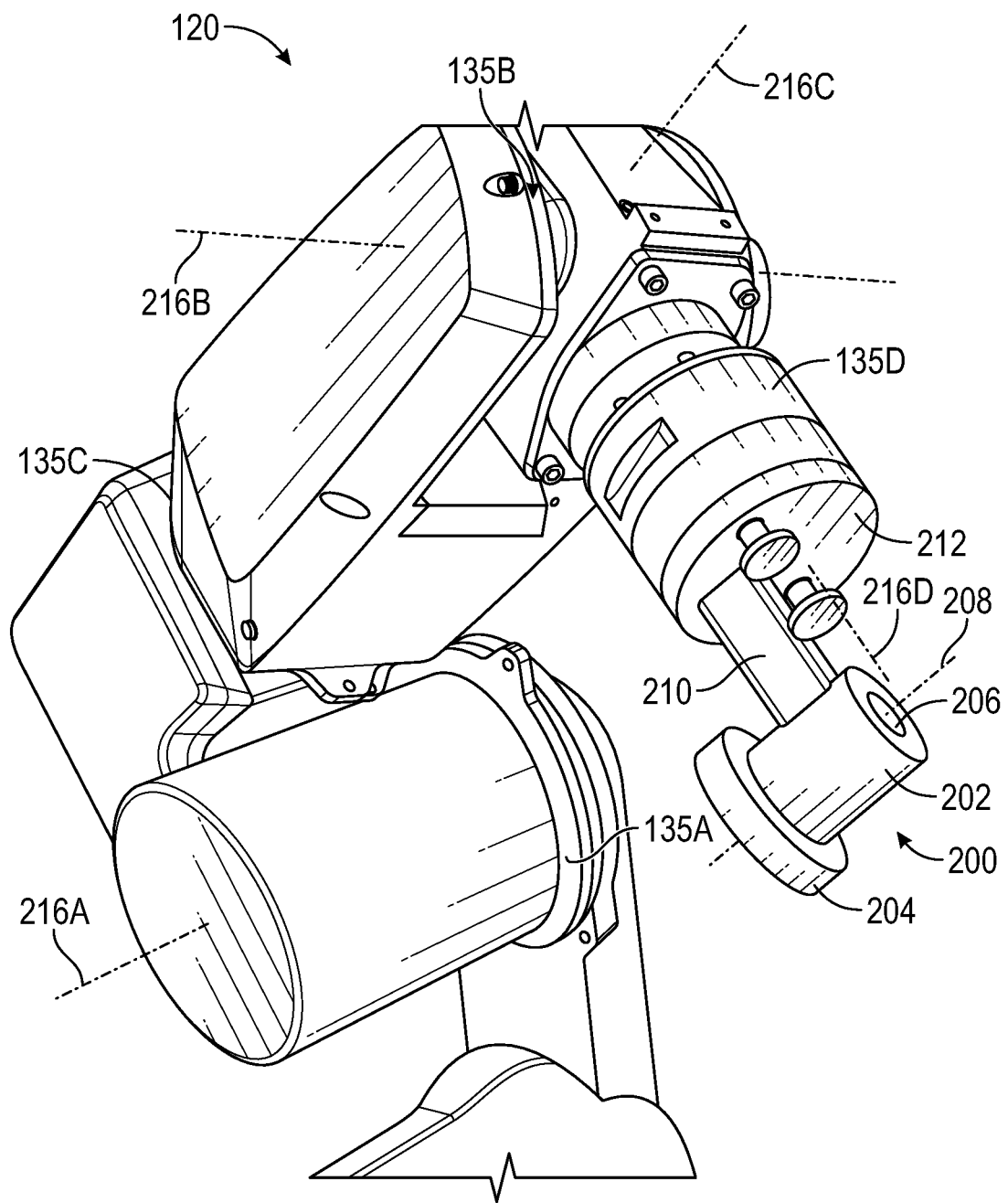
FIG. 2 is a schematic view of the robotic arm of FIG. 1 including an instrument holder configured to support or guide an instrument along an axis with an impact control device.

As discussed herein, the location where robotic arm 120 holds instruments and where associated resections or bone alterations are placed on a bone can be planned using patient-specific soft tissue information, FIG. 2 is a schematic view of robotic arm 120 of FIG. 1 including instrument holder 200, which can be positioned by robotic arm 120 relative to surgical area 105 (FIG. 1) in a known orientation, Instrument holder 200 can comprise guide body 202 and measuring device 204. Passage 206 can extend through guide body 202 and measuring device 204 along axis 208. Instrument holder 200 can be coupled to robotic arm 120 via extension 210 and mounting plate 212.

Robotic arm 120 can include joint 135A that permits rotation about axis 216A, joint 135B that can permit rotation about axis 216B, joint 135C that can permit rotation about axis 216C and joint 135D that can permit rotation about axis 216D.

In order to position instrument holder 200 relative to anatomy of patient 110 (FIG. 1), surgical system 100 (FIG. 1) can manipulate robotic arm 120 automatically by computing system 140 or a surgeon manually operating computing system 140 to move instrument holder 200 to the desired location, e.g., a location called for by a surgical plan to align an instrument relative to the anatomy. For example, robotic arm 120 can be manipulated along axes 216A-216D to position passage 208 of instrument holder 200 along a trajectory for which an instrument is to be guided.

Robotic arm 120 can be separately registered to the coordinate system of surgical system 100, such via use of a tracking element 170. Fiducial markers can additionally be separately registered to the coordinate system of surgical system 100 via engagement with a probe having a tracking element 170 attached thereto. As such, some or all of the components of surgical system 100 can be individually registered to the coordinate system and, if desired, movement of such components can be continuously or intermittently tracked with a tracking element 170.

It can be a difficult task to ensure instruments attached to robotic arm 120 are accurately aligned with and positioned relative to patient 110, particularly if the instrument needs to be individually manipulated during the procedure, such as by intervention of personnel including a surgeon. For example, sometimes robotic arm 120 is positioned to provide the proper alignment of an instrument, e.g., a guide pin, that needs to be inserted into the patient. Thus, robotic arm 120 can automatically provide a trajectory for an instrument, while the surgeon manually provides the motive force for the instrument. However, once the surgeon moves the instrument relative to robotic arm 120, robotic arm 120 typically has no influence over the movement of the instrument. However, with the present disclosure, instrument holder 200 can be provided with an impact limiting device or a force damping device to limit the force (e.g., velocity) with which the instrument can move along instrument holder 200. Accordingly, the surgical plan can include impact load information such as an upper force limit below which movement of the instrument can be constrained by instrument holder 200 to avoid damaging the bone structure of the particular patient based on the bone density of that particular patient at the specific location. In other examples, hand-held force-limiting devices can be used. Thus, the surgical plan can include bone density information that can be used to tune, program or adjust the force that instrument holder 200 or a hand-held device is configured to limit, as is discussed in greater detail below.

Figure 3A:
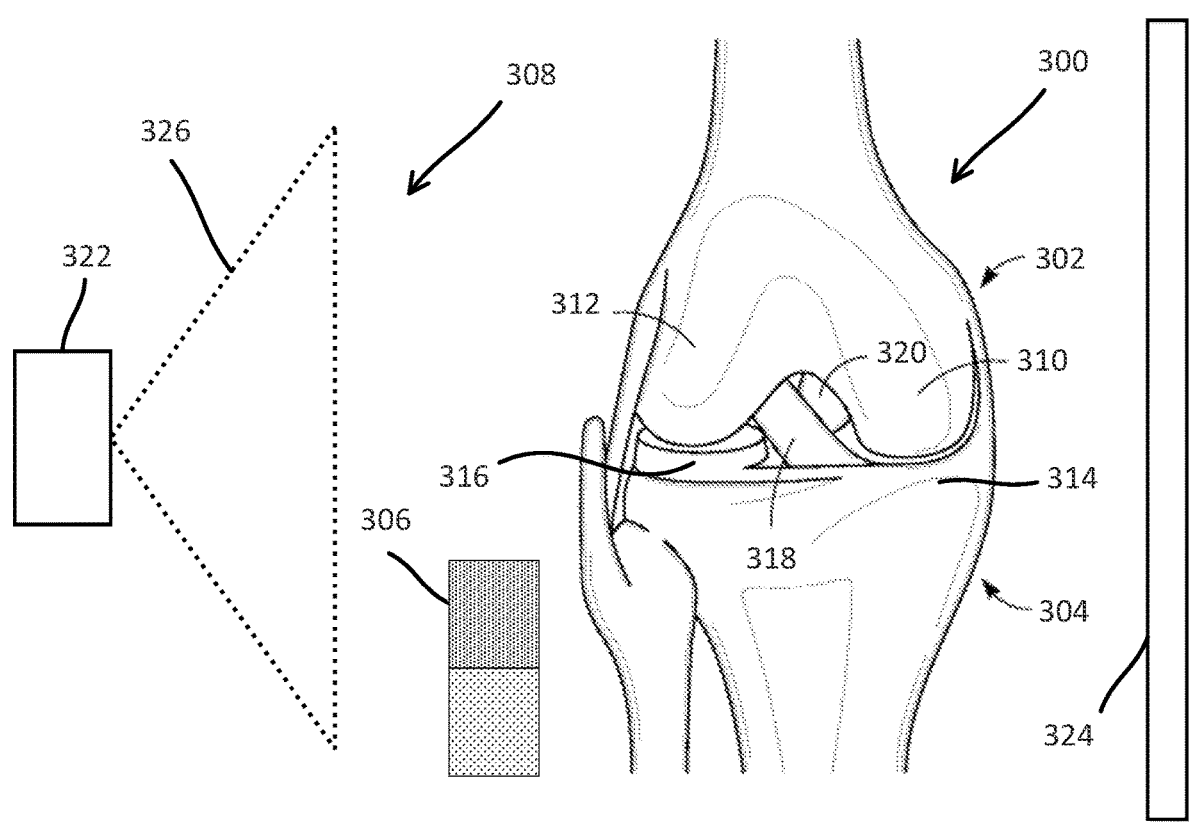
FIG. 3A is a schematic front view of a tibia and a femur of a knee joint being imaged proximate a bone density reference.
Figure 3B:
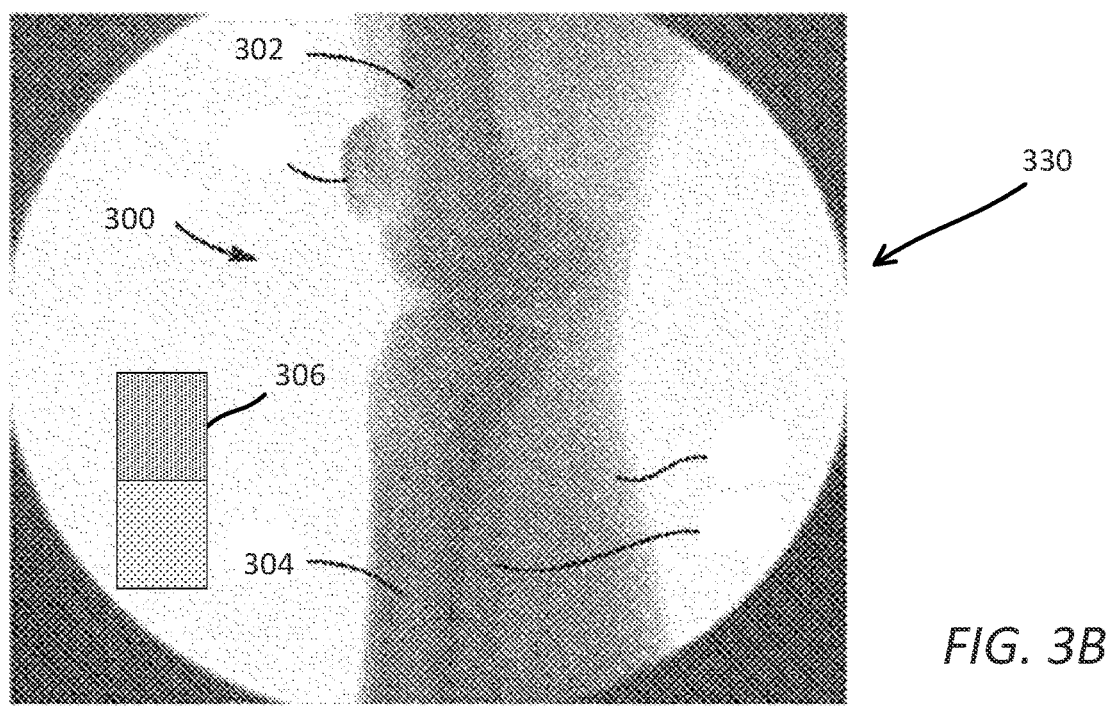
FIG. 3B is a schematic view of an x-ray image of a side of the knee joint and the bone density reference of FIG. 3A.

FIG. 3A is a perspective view of natural knee joint 300, including femur 302 and tibia 304, positioned proximate bone density marker 306 and imaging system 308. FIG. 3B is a schematic view of x-ray image 330 of knee joint 300 and bone density marker 306. FIGS. 3A and 3B are discussed concurrently. Though the present application is discussed with reference to bones of a knee joint, the systems, devices and methods of the present disclosure can be used to in conjunction with other bones and joints, such as ankle, shoulder and hip joints.

Femur 302 can include medial condyle 310 and lateral condyle 312 at a distal end of femur 302 that are shaped to mate with medial and lateral tibia condyles 314 and 316, respectively. Various soft tissues (e.g., ligaments) can be attached to femur 302 and tibia 304, For example, anterior cruciate ligament (ACL) 318 can extend from an anterior side of tibia 304 to femur 302, and posterior cruciate ligament (PCL) 320 can extend from a posterior side of tibia 304 to the femur 302. Furthermore, other soft tissue can be discerned from within x-ray image 330, such as cartilage and bone density.

In examples, imaging system 308 can comprise an x-ray imaging system including high voltage generator x-ray tube 322 and x-ray imaging detector 324, which typically comprises a digital video detector, a solid state detector, or x-ray film. However, other types of imaging systems can be used, particularly those that provide imaging relating to soft tissue. In examples, Magnetic Resonance Imaging (MRI) and ultrasound imaging systems can be used.

Femur 302 and tibia 304 can be positioned proximate imaging system 308 within the field of view of x-ray tube 322. Bone density marker 306 can additionally positioned within the field of view of x-ray tube 322. X-rays 326 emanating from x-ray tube 322 can travel through femur 302 and tibia 304, as well as simultaneously with bone density marker 306 to impinge upon the x-ray imaging detector 324. X-ray image 330 (FIG. 3B) produced by detector 324 can then pass through an amplifier and a computer for processing, or may be recorded on x-ray film in a developer. The resulting image 330 of bone density marker 306 can be compared to the resulting image of femur 302 and tibia 304.

Bone density marker 306 can comprise a reference item having a known density that corresponds to that of bone and, as such, bone density marker 306 can replicate density of healthy bone. In examples, bone density marker 306 can have varying density to indicate different degrees of density for comparison to different instances of naturally occurring density in different patients. Bone density marker 306 can 1) be made with uniform density and have increasing thickness from one end to the other, which will show up as increasing density in image 330, or 2) can be produced with increasing density from one end to the other, which will also show up as increasing density in image 330. Thus, known bone mineral densities of bone density marker 306 can be used to compare images of bone density marker 306 to images of bone to extrapolate actual or estimated bone mineral density. In examples, bone density marker 306 can comprise a block of material fabricated from a demineralized bone matrix composite. In examples, the demineralized bone matrix composite can be made according to U.S. Pat. No. 7,582,309 to Rosenberg et al., which is assigned to Etex Corporation. In examples, the demineralized bone matrix composite can be fabricated from Equivabone® Bone Graft Substitute or βBeta-bsm® Injectable Bone Substitute Material, each of which is commercially available from Zimmer Biomet.

Femur 302 and tibia 304 can have varying bone density from patient to patient, which can be visible in x-ray images. Bone density is a product of bone mineral content in the material forming the bone. Bone density can be indirectly determined or estimated by measuring the density per square unit of bone within an x-ray image. As such, healthy bone will have a density, e.g., an associated color in image 330, while diseased or damaged bone will have a different, e.g., less dense, density, which can show up in image 330 as a lighter color. For example, bone matter afflicted with osteoporosis can be less dense than healthy bone and can show up as a lighter color than healthy bone in an x-ray image. Less dense bone can be weaker than healthy bone and is, therefore, more vulnerable to breaking or cracking. For example, hip replacement procedures are particularly vulnerable to bone cracking, either directly from the implant procedure or due to long term fatigue that arises from stresses imparted dud ng the implant procedure. Thus, reduction in the amount of stress imparted to a bone during an implantation procedure can be used to reduce the occurrence of revision surgeries.

Figure 4:
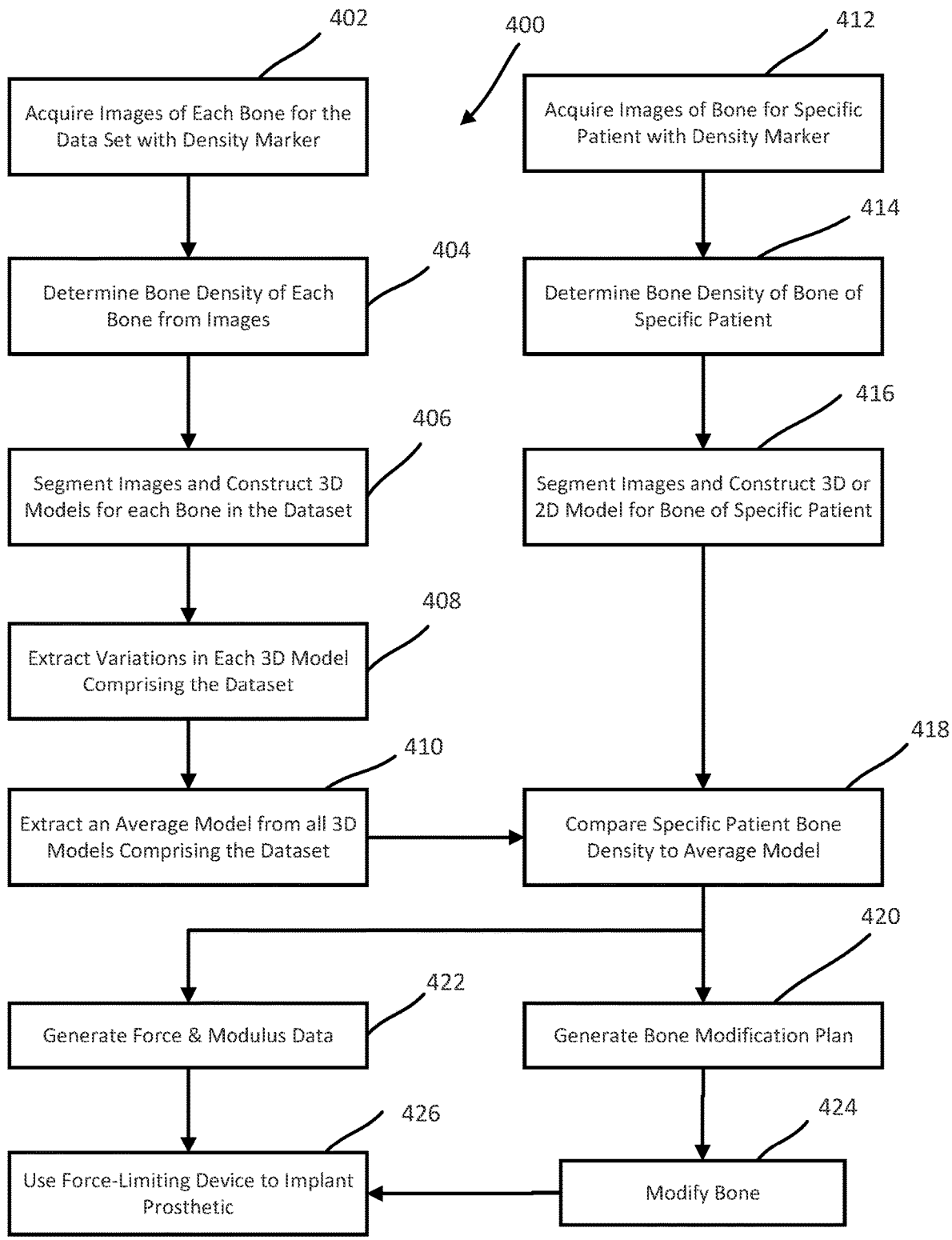
FIG. 4 is a block diagram illustrating steps of methods for generating a mean bone having patient-specific bone density information and planning an arthroplasty procedure and a patient-specific implant using patient-specific bone density information.

FIG. 4 is a block diagram illustrating steps of method 400 for generating a mean bone having patient-specific bone density information and planning an arthroplasty procedure using patient-specific bone density information. The bone model or mean bone can be a generalized model based on multiple patient bone models and can be selected from a principle component analysis ("PCA") based statistical bone atlas. The mean bone can be augmented with bone mineral density information obtained from a specific patient, such as with x-ray imaging. The mean bone augmented with a specific patient's bone mineral density information can then be used to make bone modifications for the bone to receive prosthetic implants to minimize the impact to bone structure, to fabricate patient-specific prosthetic implants having regions selectively modified to reduce engagement of hard surfaces with bone, such as weakened or brittle bone, and to generate instructions for setting force damping mechanisms that limit the capability of prosthetic implants from striking the bone during implantation procedures.

At step 402, images of bones of a plurality of patients can be obtained. Each bone can be imaged a plurality of times in different orthogonal directions, e.g., anterior, posterior, medial and lateral. A bone density marker, such as bone density marker 306, can be positioned within each image. The bone density marker can be similar in construction to bone density marker 306 discussed above. One bone density marker can be used in all of the images or a plurality of bone density markers each having the same construction can be used. However, different types of bone density markers can be used so long as the same or consistent bone mineral density information can be obtained and used in a normalized fashion. In examples, x-ray images are used because bone density information can be readily extrapolated from x-ray images, particularly when used with bone density markers. However, bone density can be determined from other imaging techniques, such as by using ultrasound densitometry or MRI.

At step 404, bone density of each bone in the plurality of bones can be determined using the density markers placed in each image. For example, coloring of the bones in each image can be compared to coloring of the bone density marker to match areas of the hone to specific bone mineral densities represented by the bone density marker. Bone density information from the different orthogonal views can be pieced together during construction of three-dimensional models for each bone. In examples, step 404 can be omitted, such that the mean bone model comprises only a mean bone shape into which patient-specific density information can be incorporated.

At step 406, a bone model can be constructed of the data set produced by the images taken from the bones of the plurality of patients, such as those taken at step 402. The bone model can be a generalized model based on multiple patient bone models and can be selected from a principle component analysis ("PCA") based statistical bone atlas. One such a priori bone atlas, formed in accordance with method 400 includes a dataset of four-hundred dry femur and tibia bone pairs, scanned by CT and segmented to create models of each bone. The method of building and using one such statistical atlas is described in MAHFOUZ M et al., "Automatic Methods for Characterization of Sexual Dimorphism of Adult Femora: Distal Femur," *Computer Methods in Biomechanics and Biomedical Engineering*, 10(6) 2007, the disclosure of which is incorporated herein by reference in its entirety. Each bone model, $M_i$, (where $I_e[1, N]$, N being the number of models in the dataset) can have the same number of vertices, wherein the vertex, $V_j$, in a select one model corresponds (at the same anatomical location on the bone) to the vertex, $V_j$, in another one model within the statistical atlas.

At step 408, PCA can then performed on each model in the dataset to extract the modes of variation of the surface of the bone. Each mode of variation is represented by a plurality of eigenvectors resulting from the PCA. The eigenvectors, sometimes called eigenbones, define a vector space of bone morphology variations extracted from the dataset. The PCA cany include any one model from the dataset, expressed as a linear combination of the eigenbones.

At step 410, an average model of all of the 3-D models comprising the dataset is extracted and can be defined as:

$$Mavg = 1N \Sigma i = 1N M i(17) M i = M avg + \Sigma k = 1L aik U k \forall i \in [1,N]$$

Where the variables are defined as follows:
Mavg=the mean bone of the dataset;
L=dimensionality of the eigenspace (i.e., the number of eigenbones) and is equal to N;
N=number of models in the data;
Uk=kth eigenbone; and
Aik=kth shape descriptor or eigenbone's coefficient for the ith model.

Furthermore, any new model, Mnew, i.e., a model not already existing in the dataset, can be approximately represented by new values of the shape descriptors (eigenvectors coefficients) as follows:

$$Mnew \cong Mavg + \Sigma k=1W ak\ U k$$

Where the variables are defined as follows:
Mnew=new bone model;
Ak=indexed shape descriptors for the new model; and
W=number of principal components to use in the model approximation, where W≤L.

The accuracy of Mnew is directly proportional to the number of principal components (W) used in approximating the new model and the number of models, L, of the dataset used for the PCA. The residual error or root mean square error ("RMS") for using the PCA shape descriptors is defined by:

$$RMS = rms[M\ new - (M\ avg + \Sigma k=1W ak\ U k)]$$

Therefore, the RMS when comparing any two different models, A and B, having the same number of vertices is defined by:

$$RMS = rms\ (A=B) = \Sigma j=1m\ \sqrt{V Aj - V Bj}\ 2\ m$$

Where VAj is the jth vertex in model A, and similarly, VBj is the jth vertex in model B.

Further description of such a bone model and associated procedures for generating a bone model are described in U.S. Pat. No. 10,512,245 to Mahfouz titled "Method and apparatus for three dimensional reconstruction of a joint using ultrasound," the contents of which are hereby incorporated in their entirety by this reference. Additional examples of generating mean bone models are described in U.S. Pat. No. 10,130,478 to Mahfouz titled "Ethnic-specific orthopaedic implants and custom cutting jig," the contents of which are hereby incorporated in their entirety by this reference.

Steps 406-410 can further incorporate bone density information determined at step 404. As such, patterns of healthy bone can be incorporated into the mean bone model to, for example, provide an indication of where a bone is relatively stronger and relatively weaker in a healthy bone. Such information can be used to plan procedures for implanting orthopedic devices. Such normalized healthy bone density information can also be compared to bone density information of a specific patient, such as can be obtained in steps 412-416, to identify areas of weakness or disease. However, as mentioned, step 404 can be omitted such that step 418 simply comprises importing of a specific-patients bone density information into a three-dimensional volume represented by the mean bone model.

At step 412, a specific patient can be imaged for comparison of bones of the specific patient to the mean bone model, A plurality of orthogonal images of the bones of the specific patient can be obtained with a density reference marker, such those described herein, in the images. As discussed, x-ray imaging can be used or other types of imaging.

At step 414, the bone density of the specific patient at different locations throughout the imaged bones can be determined by comparing the density marker in the images to the images of the bone, as is described herein.

At step 416, images of the specific patient can be segmented to construct a 3D model of the specific patient's bones. For example, a process similar to that described with reference to steps 402-410 can be used to build a bone model of only a single set of images of one bone or joint of a particular patient.

At step 418, the patient-specific bone model can be referenced to the mean bone model to facilitate understanding of the anatomy of the specific patient and to plan a surgical procedure. In a first example, the bone density of the patient-specific bone model can be compared to the bone density of the mean bone model. As such, areas of relative weakness, e.g., low bone density, of the specific patient can be identified by comparison to healthy bone of the mean bone model. Thus, a direct comparison between the two bone models can reveal areas where the bone of the specific patient is less dense or weaker than a typical bone.

In a second example, patient-specific bone density information from the patient-specific bone model can be imported into the mean bone model, wherein the mean bone model does not include aggregated bone density information. Thus, bone density information of the specific patient can be directly viewed on the mean bone model. Areas of weak or low density bone can be identified relative to other parts of the bone or to reference information indicating healthy or typical levels of bone density for a bone. In some examples, step 416 can be omitted such that bone density information from two-dimensional imaging of the specific patient can be directly incorporated into the mean bone without having to construct a three-dimensional model of the bone of the specific patient.

In additional examples, robotic system 115 can utilize artificial intelligence to identify areas of weak bone density. For example, bone density information from the patient population used to generate the mean bone model can be used to identify known areas of weak bone density and what associated weak bone areas look like in imaging. Robotic system 115 can then review the patient-specific mean bone model to identify similar patterns in the imaging that resemble the weak bone areas.

At step 420, weak or unhealthy bone can be identified in the patient-specific mean bone model, e.g., a three-dimensional bone model having the mean shape or shell of population into which bone density information of a single patient is imported. Bone modification to accept the prosthetic implant can be identified on the patient-specific mean bone model. Thus, resection planes and bone anchor bores can be directly plotted on the patient-specific mean bone model to accommodate weak or low-density bone, such as by plotting resection planes to remove weak bone or avoid weak bone or to ensure that bone anchors can be adequately fixed to bone. In examples, bone modification plotting can be electronically drawn directly onto the patient-specific mean bone model using graphical user interface tools, such as a mouse to manipulate resection planes in a graphical user interface (e.g., a video display device).

At step 422, the bone or bones of the specific patient can be modified according to the surgical plan, Thus, for example, femur 302 and tibia 304 can be resected and reamed to receive femoral component 512 and tibial component 514.

At step 424, force data for implanting femoral component 512 and tibial component 514 can be generated. For example, bone density information for the specific patient can be extracted from the patient-specific mean bone model at locations along resection planes and anchor bores. The hardness of the bone density at these locations can be determined, such as by comparing to look up tables having actual bone hardness information for different bone densities. The bone hardness information can then be used to set an upper limit for force that can be delivered to the bone to implant a prosthetic device. In turn, this information can be used to set an upper limit on force-limiting devices that can be used to limit the delivery of impact forces to bone from implantation instruments. Additionally, bone density information from the patient-specific mean bone model along the resection planes and anchor bores can be used to determine material properties for implants. For example, portions of an implant that engage bone or only portions that engage low-density bone can be modified to incorporate pads or islands of soft material to dampen impacts delivered to the bone or to prevent imparting stress into the bone. As both cases, instances of bone fracturing, and associated revision surgery, can be reduced.

Figure 6:
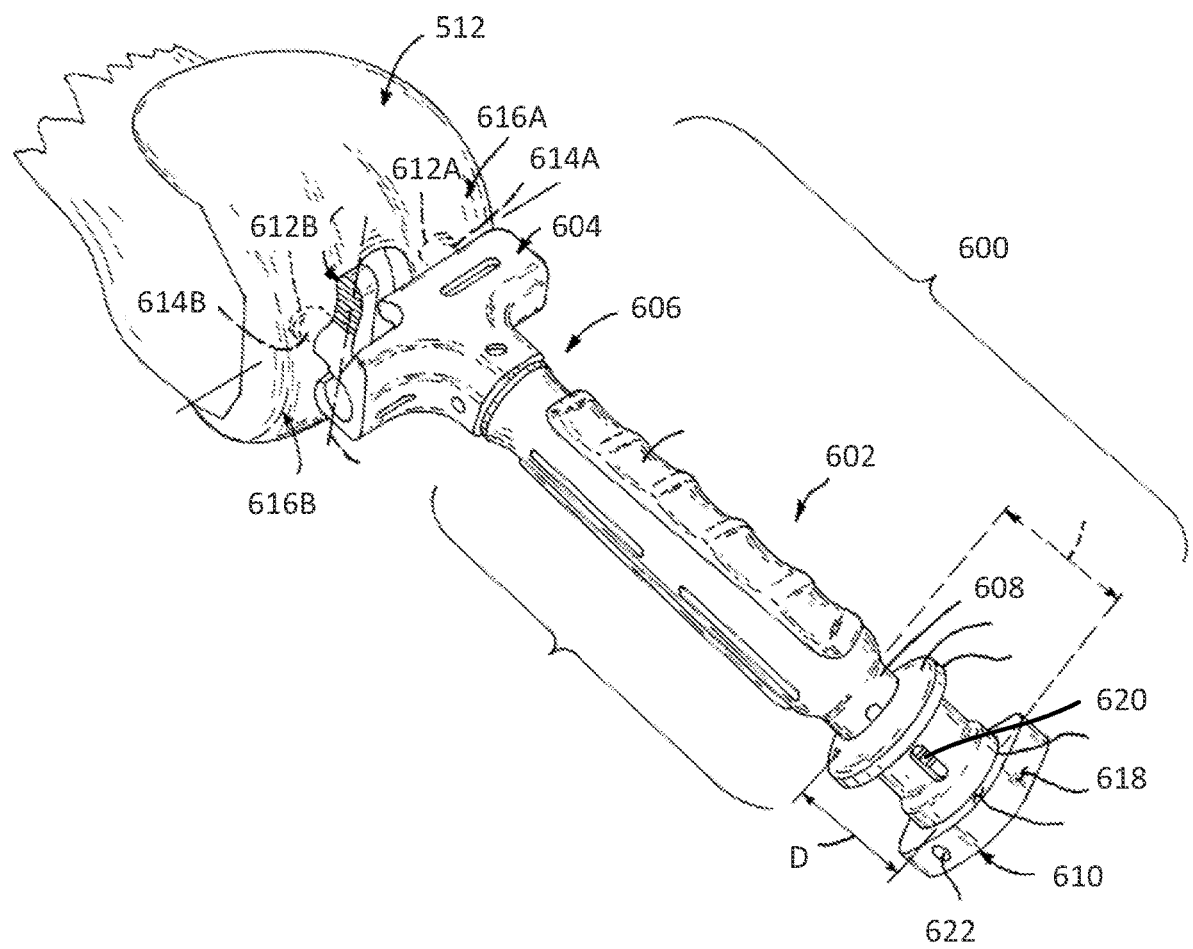
FIG. 6 is a perspective view of an impaction device that can be used, for example, with the impact control device of FIG. 2, or manually, to facilitate implanting of a prosthetic femoral implant into a femur to avoid exceeding fracture limits of the bone.

At step 426, the prosthetic components can be implanted using the force-limiting devices described herein, such as instrument holder 200 (FIG. 2) and impaction device 600 (FIG. 6).

Figure 5:
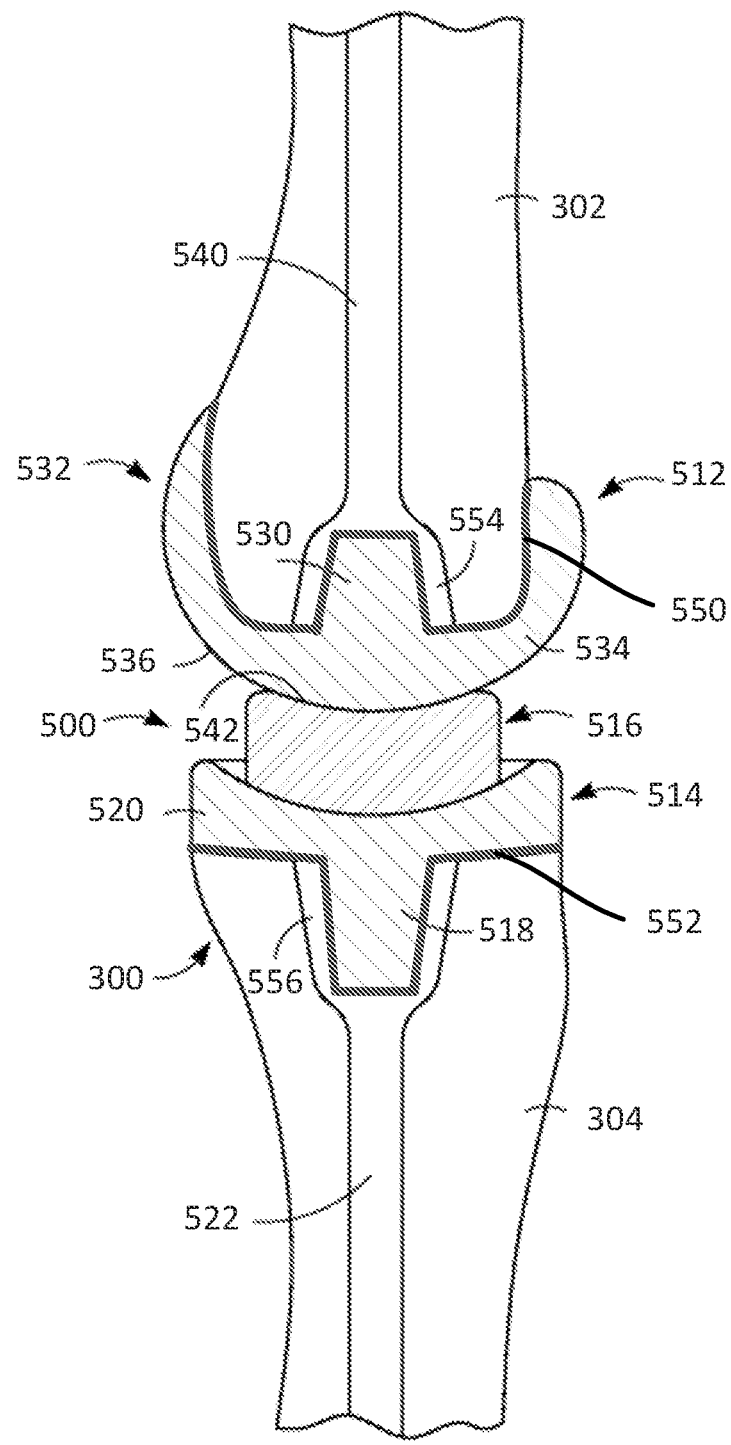
FIG. 5 is a side cross-sectional view of the knee joint of FIGS. 3A and 3B having a patient-specific total knee prosthetic implanted in the tibia and femur.

FIG. 5 is a side cross-sectional view of knee joint 300 of FIGS. 3A and 3B having patient-specific total knee prosthetic 500 ("knee prosthetic 500") implanted in femur 302 and tibia 304.

Knee prosthetic 500 can comprise femoral component 512 and tibial component 514. Tibial component 514 can be coupled to a proximal end of tibia 304 and femoral component 512 can be coupled to a distal end of femur 302. Articulation component 516 can be positioned between tibial component 514 and the femoral component 512 to provide a low-friction articulation surface for sliding motion between tibial component 514 and femoral component 512.

Tibial component 514 can comprise stem 518 and base plate 520, also sometimes referred to as a tibial platform. Stem, or anchor, 518 can be implanted into tibia 304, for example, extending into medullary canal 522 of tibia 304. Stem 518 can provide a surface or surfaces for coupling or attachment between tibial component 514 and tibia 304. Although not shown, a stem extension can be coupled to stem 518 for extending further into medullary canal 522. Base plate 520 can provide support for articulation component 516, such as within a cup or depression within base plate 520.

Femoral component 512 can comprise stem 530 and condyle portion 532 comprising generally convexly-curved anterior condyle surface 534 and posterior condyle surface 536. Stem, or anchor, 530 can be implanted into femur 304, for example, extending into medullary canal 540 of femur 302. Stem 530 can provide a surface or surfaces for coupling or attachment between femoral component 512 and femur 302. Although not shown, a stem extension can be coupled to stem 530 for extending further into medullary canal 540. Condyle surfaces 534 and 536 can interact with articulation surface 542 in order to provide a sliding relationship between femoral component 512 and articulation component 516, and in turn with tibial component 514 in order to simulate a natural knee joint (e.g., knee joint 300).

Femoral component 512 and tibial component 514 can be patient-specific to include layers that are fabricated to a specific hardness to prevent damage to the bone structure to which they are implanted. Femoral component 512 can include patient-specific layer 550 and tibial component 514 can include patient-specific layer 552. Patient-specific layers 550 and 552 can be fabricated based on bone density information taken from image 330 either directly or as incorporated into a three-dimensional model. Layers 550 and 552 can comprise layers that contact bone. In other examples, rather than providing layers 550 and 552 that extend across all resected or exposed bone surfaces, only exposed bone surfaces with low or weak density can be mated with patient-specific portions.

For example, femoral component 512 and tibial component 514, excluding layers 550 and 552 can be fabricated of typical materials for prosthetic implants, such as titanium or stainless steel. Such materials can be hard and as such are desirable to reduce wear and prevent damage or corrosion. However, such hard materials can be significantly harder than the bone material to which they are attached. As such, there is the potential for femoral component 512 and tibial component 514 to damage femur 304 and tibia 306, particularly during the implant procedures. To implant femoral component 512, medullary canal 540 can be reamed to produce cavity 554 to receive stem 530. Cavity 554 can be produced to be slightly smaller than stem 530 in order to obtain a tight fit so that femoral component 512 is not loose and likely to shift position. Likewise, to implant tibial component 514, medullary canal 522 can be reamed to produce cavity 556 to receive stem 518. Cavity 556 can be produced to be slightly smaller than stem 518 in order to obtain a tight fit so that tibial component 514 is not loose and likely to shift position. Thus, in order to implant and fully seat femoral component 512 and tibial component 514, it can be useful to impact each of femoral component 512 and tibial component 514 with a force to overcome resistance of the bone. Examples of devices for delivering such force are described with reference to FIGS. 2 and 6. However, such force can potentially cause unintended modification of femur 302 and tibia 304. For example, femur 302 and femur 304 can become cracked or damage if impacted by too high of a force, such as one that exceeds the stress limitations of the bone. Areas of a bone that have density lower than healthy bone can be especially susceptible to damage, particularly when the surgeon is unaware of bone at the impact site being weaker than normal.

In examples, patient-specific layers 550 and 552 can be fabricated from material having a lower modulus of elasticity or a lower hardness than portions of the implant intended to provide structural support or an articulation surface against which another bone or prosthetic component engages. Thus, patient-specific layers 550 and 552 can be made of a plastic material, while the remainder of the devices can be made of metal materials. In other examples, patient-specific layers 550 and 552 can be made of the same material as the remainder of the devises, but can have different properties (density and, hence, compressibility). In examples, patient-specific layers 550 and 552 can be made integral with femoral component 512 and tibial component 514, respectively, such as via additive manufacturing processes. Additive manufacturing processes, such as three-dimensional (3D) printing techniques, (such as electron beam or laser additive manufacturing) can be used to produce metallic structures of titanium alloys or stainless steel, or of plastic materials, having changing macro-properties. For example, the material can be produced with high density as an articulation surface and with low density in places that contact bone or unhealthy bone. The lower density material will act more softly than the high density material. Furthermore, additive manufacturing processes allow one or more portions of components 512 and 514 to be built directly onto one of more of the other components. As such, patient-specific layers 550 and 552 can be made of a polymeric material to provide a cushion, while condyle surfaces 534 and 536 and base plate 520 can be made of metallic material to facilitate articulation and provide structural support.

FIG. 6 is a perspective view of impaction device 600 that can be used with the impact control device 200 of FIG. 2 to facilitate implanting of femoral component 512 into femur 302. Femoral component 512 can be an instance of femoral component 512 of FIG. 5 or in other examples, impaction device 600 can be used with other femoral components. Similarly, impaction device 600 can be used with prosthetic components for other bones, such as tibial components, hip components and shoulder components.

Impaction device 600 can comprise handle 602 and inserter head 604. Handle 602 can be removably connectable at end 606 to inserter head 604 and at end 608 to impact-limiter 610. Inserter head 604 can include couplers 612A and 612B for insertion into coupling ports 614A and 614B of femoral component 512 to couple medial condyle 616A and lateral condyle 616B of femoral component 512 to inserter head 604.

Impact-limiter 610 can comprise impact base 618, which is configured to struck by an impact tool, such as a hammer or the like. Impact-limiter 610 can include damping device 620 that can be configured to absorb energy from an impact delivered to impact base 618. Impact base 618 can be displaced in the direction of handle 602 distance D. Distance D can become temporarily reduced as damping device 620 is displaced to absorb energy and impact base 618 moves toward handle 602. Damping device 620 can increase the time it takes for distance D to be traveled such that less force is transmitted to handle 602 from impact base 618, e.g., the velocity of impact base 618 is reduced at the end of traversing distance D so that less energy is delivered to handle 602. Damping device 620 can include a spring to return impact device 620 to the original position. Impact-limiter 610 can be adjusted via adjustment port 622 to tune the amount of force that damping device 620. In examples, damping device 620 can comprise a magnetorheological damper or a magnetorheological shock absorber. Magnetorheological devices can be filled with a magnetorheological fluid manipulated by a magnet to adjust the shock absorbing characteristics of the fluid. Viscosity of the magnetorheological fluid can increase when subject to magnetic fields of increasing intensity. In other examples, impact-limiter 610 can comprise a spring-biased device where the stiffness of the spring can be increased to transmit a greater amount of force through the device. As such, a surgeon can consult the patient-specific bone density of a particular patient into which femoral component 512 is to be attached. If it is determined by the surgeon that the patient has particularly low density bone around the implant site for femoral component 512, damping device 620 can be adjusted, such as by inserting a screwdriver into adjustment port 622, to increase the damping effect produced by impact-limiter 610.

In another example of the present disclosure, impact device 600 can be used without impact-limiter 610 such that end 608 can be directly impacted, such as with a hammer. Impact device 600 can be loaded into instrument holder 200 of FIG. 2 that can be configured to include an impact-limiter. Such an impact limiter can engage with handle 602 to limit the speed with which impact device 600 can move through instrument holder 200. Computing system 140 can be provided with calibration information for the impact-limiting device as well as bone density information and associated safe levels of impaction forces, (e.g., kg m/s^2) that can impact the bone without causing fracture. Computing system 140 can also be provided with information relating to the size and weight of various impaction devices (e.g., impact device 600 and hammers). As such, bone density information for a specific patient can be entered into computing system 140, and computing system 140 can adjust the impact-limiting device of instrument holder 200 to provide damping so that a given impacting system (impact device and hammer) will not produce a force above a threshold determined by computing system 140.

Figure 7:
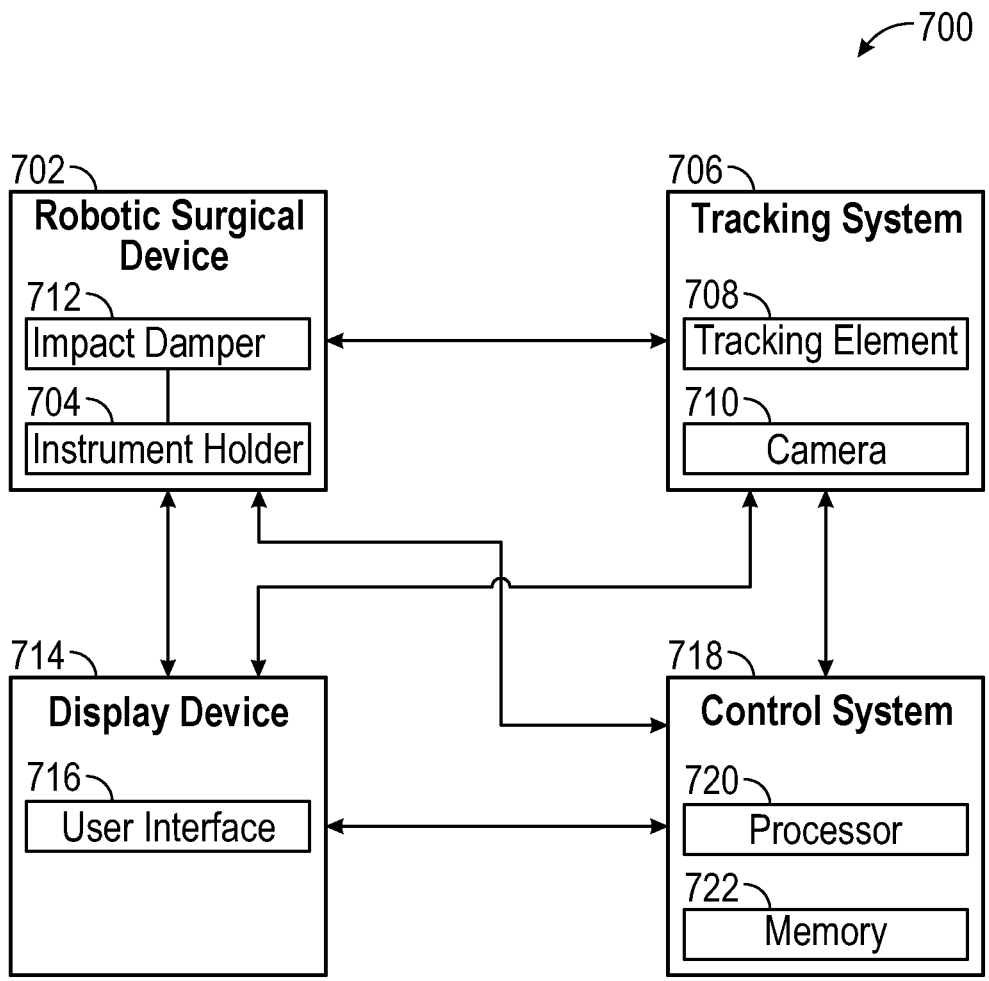
FIG. 7 is a schematic illustration of a robotic surgical system incorporating a bone model enhanced with bone-density information and an impact control device of the present application interacting with a tracking system.

FIG. 7 illustrates system 700 for performing techniques described herein, in accordance with some embodiments. System 700 is an example of a system that can incorporate surgical system 100 of FIG. 1. System 700 can include robotic surgical device 702 (e.g., robotic surgical device 115) coupled to instrument holder 704 (e.g., instrument holder 200 of FIG. 2), which may interact with tracking system 706. In other examples, the instrument holders described herein can be used without tracking system 706. Tracking system 706 can include tracking element 708, camera 710 and registration device 711 (e.g., pointer 326). Instrument holder 704 (e.g., instrument holder 200) can include impact dampers 712 (e.g., a spring-biased device or a magnetorheological device). System 700 can include display device 714, which can be used to display user interface 716. System 700 can include control system 718 (e.g., a robotic controller or computing system 140 of FIG. 1), including processor 720 and memory 722. In an example, display device 714 can be coupled to one or more of robotic surgical device 702, tracking system 706, or control system 718. As such, data generated by impact damper 712 (e.g., force delivered to and arrested by impact damper 712) can be shared with control system 718, tracking system 706 and an operator of system 700 via display device 714. In examples, instrument holder 704 can be operated without input from tracking system 708, after a registration process, such that robotic surgical device 702 can be positioned and tracked by movement of robotic arm 120 within the native coordinate system of robotic arm 120. Once in a desired position, instrument holders 704 and impact dampers 712 can be freely used by a surgeon without tracking system 706 required to reacquire position information for robotic surgical device and without control system 718 losing track of the location of robotic surgical device 702.

Control system 718 can additionally include within memory 722 information (e.g., electronic data encoded in a non-transitory computer storage medium) relating to look-up tables for bone density information of bone density marker 306, anatomic bone density information for healthy and diseased bone such as can be aggregated from bone information of sample populations, damping information for impact damper 712, and size and weight information for various prosthetic implants and devices, instruments and tools for implanting such implants and devices. Thus, control system 718 can compute bone density of a particular patient, such as by consulting a patient-specific mean bone model, calculate resection plane or anchoring bore locations within the patient-specific mean bone model, determine impact threshold for bone at the resection planes or anchoring bore locations, calculate force information for particular bone implanting and impacting devices to be used to implant a particular prosthetic component, and provide impact damping information for particular impact-limiting devices to prevent undesirable (e.g., forces capable of fracturing or stressing bone structure) forces from being delivered to a bone.

Figure 8:
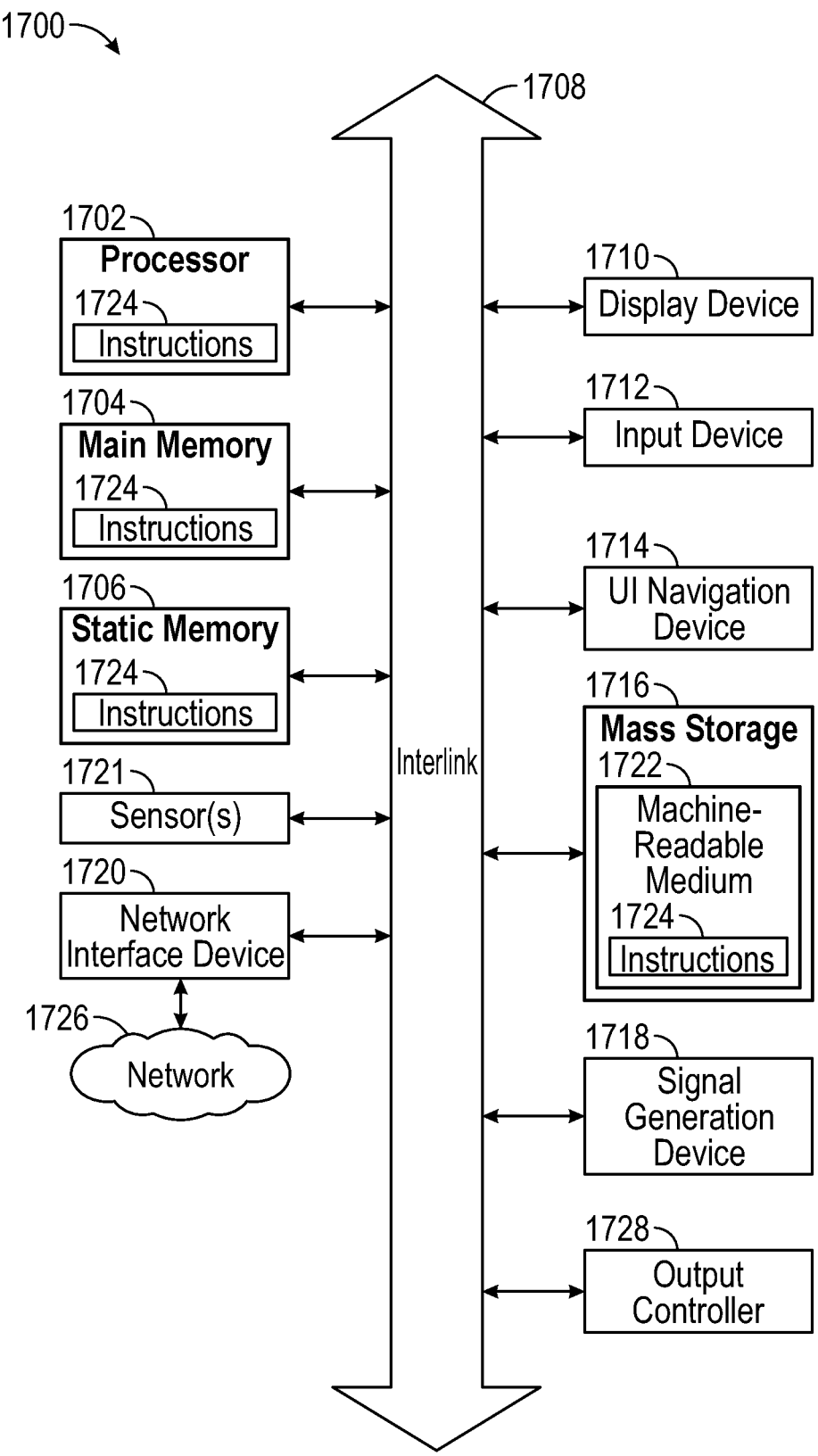
FIG. 8 is a block diagram of an example machine upon which any one or more of the techniques discussed herein may be performed and with which any of the devices discussed herein may be used in accordance with some embodiments.

FIG. 8 illustrates a block diagram of an example machine 1700 upon which any one or more of the techniques discussed herein may be performed in accordance with some embodiments. For example, machine 1700 can comprise computing system 140 of FIG. 1. Machine 1700 can comprise an example of a controller for robotic system 115 and sensors 1721 can include tracking elements 170 and 708. As such instructions 1724 can be executed by processor 1702 to generate and correlate position and orientation information to determine the position and orientation of a surgical instrument relative to robotic arm 120. For example, position information of instrument holder 200 via connection to robotic arm 120 can be stored in main memory 1704 and accessed by processor 1702. Processor 1702 can also receive input (such as at input device 1712) relating to the position of tibia 304 and femur 302 relative to robotic arm 120 via tracking devices 170 and 708, which can be stored in main memory 1704. As such, machine 1700 can continuously track and update the location of said components relative to robotic arm 120 via movement of robotic arm 120, tracking devices 170 and 708 and, for example, display said position on display device 1710 (e.g., user interface devices 145).

In alternative embodiments, machine 1700 may operate as a standalone device or may be connected (e.g., networked) to other machines. In a networked deployment, machine 1700 may operate in the capacity of a server machine, a client machine, or both in server-client network environments. In an example, machine 1700 may act as a peer machine in peer-to-peer (P2P) (or other distributed) network environment. Machine 1700 may be a personal computer (PC), a tablet PC, a set-top box (STB), a personal digital assistant (PIM), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Machine (e.g., computer system) 1700 may include hardware processor 1702 (e.g., a central processing unit (CPU), a graphics processing unit (GPU), a hardware processor core, or any combination thereof), main memory 1704 and static memory 1706, some or all of which may communicate with each other via interlink (e.g., bus) 1708. Machine 1700 may further include display unit 1710, alphanumeric input device 1712 (e.g., a keyboard), and user interface (UI) navigation device 1714 (e.g., a mouse). In an example, display unit 1710, input device 1712 and UI navigation device 1714 may be a touch screen display. Machine 1700 may additionally include storage device (e.g., drive unit) 1716, signal generation device 1718 (e.g., a speaker), network interface device 1720, and one or more sensors 1721, such as a global positioning system (GPS) sensor, compass, accelerometer, or other sensor. Machine 1700 may include output controller 1728, such as a serial (e.g., Universal Serial Bus (USB), parallel, or other wired or wireless (e.g., infrared (IR), near field communication (NFC), etc.) connection to communicate or control one or more peripheral devices (e.g., a printer, card reader, etc.). Sensors 1721 can also include impact-limiting devices described herein. Thus, a user can input a specific patient's bone density using input device 1712, processor 1702 can consult stock bone density information stored in memory 1706 and generate settings for an impact-limiting device that can sense force being delivered by an object. Likewise, output of force delivered to said object can be output by sensor 1721 and displayed at display device 1710 or stored in memory 1706. Furthermore, system 1700 can be configured to display force information at display device 1710 to provide real-time feedback to a user when force being delivered to a specific patient's bone is nearing, at or exceeding desirable force limits to avoid generating undue stress or cracking.

Storage device 1716 may include machine readable medium 1722 on which is stored one or more sets of data structures or instructions 1724 (e.g., software) embodying or utilized by any one or more of the techniques or functions described herein. Instructions 1724 may also reside, completely or at least partially, within main memory 1704, within static memory 1706, or within hardware processor 1702 during execution thereof by machine 1700. In an example, one or any combination of hardware processor 1702, main memory 1704, static memory 1706, or storage device 1716 may constitute machine readable media.

While machine readable medium 1722 is illustrated as a single medium, the term "machine readable medium" may include a single medium or multiple media (e.g., a centralized or distributed database, and/or associated caches and servers) configured to store the one or more instructions 1724. The term "machine readable medium" may include any medium that is capable of storing, encoding, or carrying instructions for execution by machine 1700 and that cause machine 1700 to perform any one or more of the techniques of the present disclosure, or that is capable of storing, encoding or carrying data structures used by or associated with such instructions. Non-limiting machine readable medium examples may include solid-state memories, and optical and magnetic media.

Instructions 1724 may further be transmitted or received over communications network 1726 using a transmission medium via network interface device 1720 utilizing any one of a number of transfer protocols (e.g., frame relay, internet protocol (IP), transmission control protocol (TCP), user datagram protocol (MP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, peer-to-peer (P2P) networks, among others. In an example, network interface device 1720 may include one or more physical jacks (e.g., Ethernet, coaxial, or phone jacks) or one or more antennas to connect to communications network 1726. In an example, network interface device 1720 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by machine 1700, and includes digital or analog communications signals or other intangible medium to facilitate communication of such software.

The systems, devices and methods discussed in the present application can be useful in performing prosthetic component procedures to provide better fit and comfort for the patient as well as reducing the potential for unintentionally causing damage to bones into which the prosthetic component is implanted. Such procedures can be manual or robot-assisted. In either scenario, bone density information can be used to identify weak or unhealthy bone to plan removal of unhealthy bone and plan implanting of the prosthetic component at healthy bone. Bone density information can additionally be used to accommodate unhealthy bone when it is not possible or acceptable to completely remove or work around unhealthy bone. For example, if it is determined that unhealthy bone should be left in place, then prosthetic devices can be designed and used to improve interfacing with weakened bone and the implantation process can be adapted to minimize trauma to the diseased bone. Prosthetic devices can be produced having softer layers or pads to interface with lower-density bone and prosthetic devices can be implanted with less force when being implanted in lower-density bone and to reduce the likelihood of delivering a blow to such bone that could potentially damage the lower-density bone.

In various aspects, the present disclosure can 1) help a surgeon identify weak bone so the surgeon can be aware of the weak bone and take appropriate precautions (e.g., avoid delivering blows with elevated force), 2) facilitate planning bone modifications where prosthetic implants will avoid engaging weakened or low density bone, and 3) provide information to limit the amount of force delivered to a bone with an impact limiting device or with bone-engaging material of an implanted component.

EXAMPLES

Example 1 is a method of implanting a prosthetic component using bone density information, the method comprising: positioning a bone mineral density reference proximate a patient; obtaining two-dimensional x-ray images of a bone of the patient including the bone mineral density reference; determining a density of the bone from the bone mineral density reference in the two-dimensional x-ray images; superimposing the density of the bone into a three-dimensional mean bone model to generate a patient-specific mean bone model; determining an interface between the bone and the prosthetic component based on bone density information of the patient-specific mean bone model; and implanting the prosthetic component in the bone at the interface.

In Example 2, the subject matter of Example 1 optionally includes wherein determining the interface between the bone and the prosthetic component based on bone density information of the patient-specific mean bone model comprises: evaluating portions of the bone where diseased or unhealthy bone is located; and locating the interface to avoid diseased or unhealthy bone.

In Example 3, the subject matter of Example 2 optionally includes wherein: the interface comprises a resection plane to remove a portion of the bone that includes diseased or unhealthy bone to leave healthy bone exposed along the resection plane; and the prosthetic implant includes a surface to engage the resection plane.

In Example 4, the subject matter of any one or more of Examples 2-3 optionally include wherein: the interface comprises a bore to remove a portion of the bone that includes diseased or unhealthy bone to leave healthy bone exposed along the bore; and the prosthetic implant includes an anchoring component to extend into the bore.

In Example 5, the subject matter of any one or more of Examples 1-4 optionally include wherein determining the interface between the bone and the prosthetic component based on bone density information of the patient-specific mean bone model comprises: evaluating bone density along the interface; and determining an impact load threshold for the bone at the interface to avoid damaging the bone.

In Example 6, the subject matter of Example 5 optionally includes wherein implanting the prosthetic component comprises: using a robotically-assisted alignment guide to position the prosthetic component; manually impacting the prosthetic implant in the alignment guide; and dampening movement of the prosthetic implant with an impact arrestor in the robotically-assisted alignment guide to prevent exceeding the impact load threshold.

In Example 7, the subject matter of any one or more of Examples 5-6 optionally include wherein implanting the prosthetic component comprises: manually aligning the prosthetic component along the interface; manually impacting the prosthetic implant in the alignment guide; and dampening movement of the prosthetic implant with an impact arrestor in a hand-held impact tool to prevent exceeding the impact load threshold.

In Example 8, the subject matter of any one or more of Examples 1-7 optionally include wherein determining the interface between the bone and the prosthetic component based on bone density information of the patient-specific mean bone model comprises: evaluating bone density along the interface; and determining a modulus for the prosthetic implant at the interface to avoid damaging the bone.

In Example 9, the subject matter of Example 8 optionally includes wherein the modulus for the prosthetic implant is below a below a hardness of the bone at the interface.

In Example 10, the subject matter of any one or more of Examples 8-9 optionally include designing the prosthetic implant, to have an interface layer comprising the modulus and an articulation layer configured to engage an opposing bone or opposing prosthetic, wherein the articulation layer is harder than the interface layer.

Example 11 is a method of generating an electronic surgical plan using a patient-specific bone density model, the method comprising: obtaining two-dimensional x-ray images of a bone of a patient including a bone density reference object; determining bone density levels of the bone in each of the two-dimensional x-ray images from the bone density reference object; generating a three-dimensional bone model of the bone of the patient from the two-dimensional x-ray images; importing the bone density levels into the three-dimensional model to generate three-dimensional bone density information; superimposing the three-dimensional bone density information onto a three-dimensional mean bone model to generate the patient-specific bone density model; plotting an interface for a prosthetic component on the patient-specific bone density model; and saving a digital version of the electronic surgical plan in a computer-readable storage medium.

In Example 12, the subject matter of Example 11 optionally includes wherein plotting the interface for the prosthetic component on the patient-specific bone density model comprises plotting one or more resection planes to avoid diseased bone.

In Example 13, the subject matter of Example 12 optionally includes programming a robotic surgical system with the electronic surgical plan to provide robotic guidance to a user in resecting along the interface during a surgery.

In Example 14, the subject matter of any one or more of Examples 11-13 optionally include wherein plotting the interface for the prosthetic component on the patient-specific bone density model comprises placing one or more bores for a corresponding number of anchoring components of the prosthetic component such that the one or more bores avoid diseased bone.

In Example 15, the subject matter of any one or more of Examples 11-14 optionally include wherein plotting the interface for the prosthetic component on the patient-specific bone density model comprises determining a modulus of elasticity of an interface layer of the prosthetic component that engages the interface, wherein the modulus of elasticity is configured to absorb impacts to an outer articulating surface of the prosthetic component.

In Example 16, the subject matter of Example 15 optionally includes fabricating the prosthetic component using a three-dimensional manufacturing process to include the interface layer and the outer articulating surface, wherein the outer articulating surface is harder than the interface layer.

Example 17 is a method of electronically planning a surgical procedure for implanting a prosthetic component into a bone using bone density information to reduce fracture risk, the method comprising: determining bone density of the bone in each of a plurality of two-dimensional x-ray images of the bone using a bone density reference object in the two-dimensional x-ray images; determining a three-dimensional bone density of the bone from the two-dimensional x-ray images; superimposing the three-dimensional bone density of the bone into an electronic three-dimensional mean bone model to generate an electronic patient-specific mean bone model; displaying the electronic patient-specific mean bone model on an electronic graphical display device; plotting an interface between the bone and the prosthetic component on the electronic patient-specific mean bone model in the electronic graphical display device; using the three-dimensional bone density on the electronic patient-specific mean bone model to determine a threshold impact load for the bone at the interface to avoid damaging the bone; and generating an electronic output of the threshold impact load.

In Example 18, the subject matter of Example 17 optionally includes loading the electronic output of the threshold impact load into a robotic surgical system configured to limit impacting of an implant tool based on the electronic output.

In Example 19, the subject matter of any one or more of Examples 17-18 optionally include importing bone density information from the plurality of two-dimensional x-ray images into an electronic three-dimensional model of the bone to generate three-dimensional bone density information.

In Example 20, the subject matter of any one or more of Examples 17-19 optionally include manually adjusting an impact limiter on an impacting device using the threshold impact load.

In Example 21, the subject matter of any one or more of Examples 17-20 optionally include programming a controller for a surgical robot, the controller comprising a non-transitory storage medium having computer-readable instructions stored therein comprising: the threshold impact load; the three-dimensional bone density of the bone; and mass information for impacting devices used to implant the prosthetic component.

Each of these non-limiting examples can stand on its own, or can be combined in various permutations or combinations with one or more of the other examples.

VARIOUS NOTES

The above detailed description includes references to the accompanying drawings, which form a part of the detailed description. The drawings show, by way of illustration, specific embodiments in which the invention can be practiced. These embodiments are also referred to herein as "examples," Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not 13," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMS), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. A method of implanting a prosthetic implant using bone density information, the method comprising:
   positioning a bone mineral density reference proximate a patient;
   obtaining two-dimensional x-ray images of a bone of the patient including the bone mineral density reference, wherein the two-dimensional x-ray images comprise single energy x-ray images;
   determining a density of the bone from the bone mineral density reference in the two-dimensional x-ray images;
   superimposing the density of the bone into a three-dimensional mean bone model to generate a patient-specific mean bone model, wherein a shape of the three-dimensional mean bone model comprises a mean shape of a population of bone shapes;
   determining an interface between the bone and the prosthetic implant based on bone density information of the patient-specific mean bone model; and
   implanting the prosthetic implant in the bone at the interface.

2. The method of claim 1, wherein determining the interface between the bone and the prosthetic implant based on bone density information of the patient-specific mean bone model comprises:
   evaluating portions of the bone where diseased or unhealthy bone is located; and
   locating the interface to avoid diseased or unhealthy bone.

3. The method of claim 2, wherein:
   the interface comprises a resection plane to remove a portion of the bone that includes diseased or unhealthy bone to leave healthy bone exposed along the resection plane; and the prosthetic implant includes a surface to engage the resection plane.

4. The method of claim 2, wherein:
the interface comprises a bore to remove a portion of the bone that includes diseased or unhealthy hone to leave healthy bone exposed along the bore; and
the prosthetic implant includes an anchoring component to extend into the bore.

5. The method of claim 1, wherein determining the interface between the bone and the prosthetic implant based on bone density information of the patient-specific mean bone model comprises:
evaluating bone density along the interface; and
determining an impact load threshold for the bone at the interface to avoid damaging the bone.

6. The method of claim 5, wherein implanting the prosthetic implant comprises:
using a robotically-assisted alignment guide to position the prosthetic implant;
manually impacting the prosthetic implant in the robotically-assisted alignment guide; and
dampening movement of the prosthetic implant with an impact arrestor in the robotically-assisted alignment guide to prevent exceeding the impact load threshold.

7. The method of claim 5, wherein implanting the prosthetic implant comprises:
manually aligning the prosthetic implant along the interface;
manually impacting the prosthetic implant; and
dampening movement of the prosthetic implant with an impact arrestor in a hand-held impact tool to prevent exceeding the impact load threshold.

8. The method of claim 1, wherein determining the interface between the bone and the prosthetic implant based on bone density information of the patient-specific mean bone model comprises:
evaluating bone density along the interface; and
determining a modulus for the prosthetic implant at the interface to avoid damaging the bone.

9. The method of claim 8, wherein the modulus for the prosthetic implant is below a hardness of the bone at the interface.

10. The method of claim 8, further comprising designing the prosthetic implant to have an interface layer comprising the modulus and an articulation layer configured to engage an opposing bone or opposing prosthetic, wherein the articulation layer is harder than the interface layer.

11. The method of claim 1, wherein bone mineral density reference object comprises a block of material fabricated from a demineralized bone matrix composite.

12. A method of generating an electronic surgical plan using a patient-specific bone density model, the method comprising:
obtaining two-dimensional x-ray images of a bone of a patient including a bone density reference object, wherein bone mineral density reference object comprises a block of material fabricated from a demineralized bone matrix composite;
determining bone density levels of the bone in each of the two-dimensional x-ray images from the bone density reference object;
generating a three-dimensional bone model of the bone of the patient from the two-dimensional x-ray images;
importing the bone density levels into the three-dimensional bone model to generate three-dimensional bone density information;
superimposing the three-dimensional bone density information onto a three-dimensional mean bone model to generate the patient-specific bone density model;
plotting an interface for a prosthetic component on the patient-specific bone density model; and
saving a digital version of the electronic surgical plan in a computer-readable storage medium.

13. The method of claim 12, wherein plotting the interface for the prosthetic component on the patient-specific bone density model comprises plotting one or more resection planes to avoid diseased bone.

14. The method of claim 13, further comprising programming a robotic surgical system with the electronic surgical plan to provide robotic guidance to a user in resecting along the interface during a surgery.

15. The method of claim 12, wherein plotting the interface for the prosthetic component on the patient-specific bone density model comprises placing one or more bores for a corresponding number of anchoring components of the prosthetic component such that the one or more bores avoid diseased bone.

16. The method of claim 12, wherein plotting the interface for the prosthetic component on the patient-specific bone density model comprises determining a modulus of elasticity of an interface layer of the prosthetic component that engages the interface, wherein the modulus of elasticity is configured to absorb impacts to an outer articulating surface of the prosthetic component.

17. The method of claim 16, further comprising fabricating the prosthetic component using a three-dimensional manufacturing process to include the interface layer and the outer articulating surface, wherein the outer articulating surface is harder than the interface layer.

18. The method of claim 12, wherein the block of material comprises a synthetic bone substitute material.

19. The method of claim 12, wherein a shape of the three-dimensional mean bone model comprises a mean shape of a population of bone shapes.

20. A method of electronically planning a surgical procedure for implanting a prosthetic component into a bone using bone density information to reduce fracture risk, the method comprising:
determining bone density of the bone in each of a plurality of two-dimensional x-ray images of the bone using a bone density reference object in the two-dimensional x-ray images;
determining a three-dimensional bone density of the bone from the two-dimensional x-ray images;
superimposing the three-dimensional bone density of the bone into an electronic three-dimensional mean bone model to generate an electronic patient-specific mean bone model;
displaying the electronic patient-specific mean bone model on an electronic graphical display device;
plotting an interface between the bone and the prosthetic component on the electronic patient-specific mean bone model in the electronic graphical display device;
using the three-dimensional bone density on the electronic patient-specific mean bone model to determine a threshold impact load for the bone at the interface to avoid damaging the bone; and
generating an electronic output of the threshold impact load.

21. The method of claim 20, further comprising loading the electronic output of the threshold impact load into a robotic surgical system configured to limit impacting of an implant tool based on the electronic output.

22. The method of claim 20, further comprising importing bone density information from the plurality of two-dimensional x-ray images into an electronic three-dimensional model of the bone to generate three-dimensional bone density information.

23. The method of claim 20, further comprising manually adjusting an impact limiter on an impacting device using the threshold impact load.

24. The method of claim 20, further comprising programming a controller for a surgical robot, the controller comprising a non-transitory storage medium having computer-readable instructions stored therein comprising:
- the threshold impact load;
- the three-dimensional bone density of the bone; and
- mass information for impacting devices used to implant the prosthetic component.

* * * * *